United States Patent [19]

Klutchko et al.

[11] 4,001,224
[45] Jan. 4, 1977

[54] 4-SUBSTITUTED-2, 3-DIHYDRO-1-BENZOXEPIN-3, 5-DIONES AND TAUTOMERS

[75] Inventors: Sylvester Klutchko, Hackettstown; Max von Strandtmann, Rockaway, both of N.J.

[73] Assignee: Warner-Lambert Company, Morris Plains, N.J.

[22] Filed: Mar. 18, 1976

[21] Appl. No.: 667,916

Related U.S. Application Data

[62] Division of Ser. No. 554,876, March 3, 1975.

[52] U.S. Cl. .......................... 260/240 R; 260/333; 260/293.80
[51] Int. Cl.[2] ............. C07D 313/08; C07D 405/12
[58] Field of Search ........... 260/240 R, 293.80, 333

[56] References Cited
UNITED STATES PATENTS

3,927,034 12/1975 Sawaki et al. ............. 260/240 R X

OTHER PUBLICATIONS

Chem. Abs. 3477e, vol. 64, 1966.

*Primary Examiner*—Allen B. Curtis
*Attorney, Agent, or Firm*—Albert H. Graddis; Frank S. Chow

[57] ABSTRACT

Compounds of the formula:

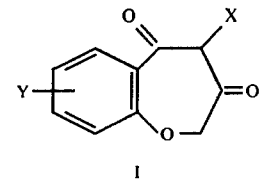

I are disclosed. In this structural formula X is

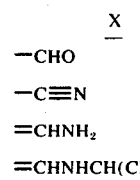

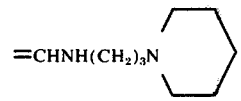

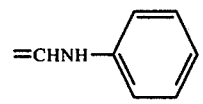

or

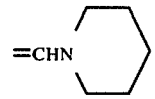

and Y is hydrogen, lower alkyl, hydroxy, lower alkoxy, chloro, bromo or aryl. Included within the scope of this invention are tautomers of the above compound. These compounds and their tautomers are indicated in the management of allergic manifestations such as bronchial asthma.

4 Claims, No Drawings

4-SUBSTITUTED-2, 3-DIHYDRO-1-BENZOXEPIN-3, 5-DIONES AND TAUTOMERS

This is a division, of application Ser. No. 554,876 filed Mar. 3, 1975.

The present invention relates to 4-substituted-2,3-dihydro-1-benzoxepin-3,5-diones, having the following structural formula:

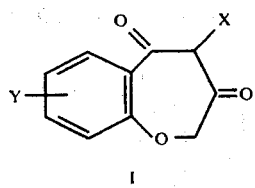

wherein X is

X
—CHO
—C≡N
=CHNH₂
=CHNHCH(CH₃)₂

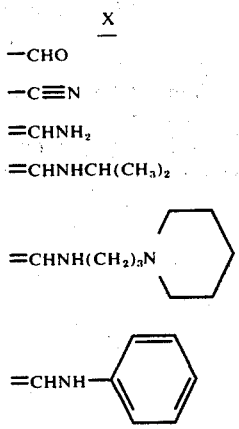

and Y is hydrogen, lower alkyl, hydroxy, lower alkoxy, chloro, bromo or aryl. Included within the scope of this invention are tautomers of the above compounds.

The compounds of this invention and their tautomers exhibit anti-allergic properties. For example, in tests conducted according to the procedures of I. Mota, *Life Sciences*, 7, 465 (1963) and Z. Ovary, O. Bier, *Proc. Soc. Exptl. Biol. Med.*, 81, 584 (1952), these compounds were effective in preventing allergic and asthmatic reactions in rats at a dose of about 25 mg/kg intraperitoneally. These compounds are indicated in the management of allergic conditions such as asthma, hay fever and the like in mammals such as men.

Generally speaking, a dose of 25 mg/kg orally or by injection is indicated to provide symptomatic relief.

To use these compounds, they are formulated with known pharmaceutical excipients such as lactose, water for injection, into dosage forms such as tablets or injections for intramuscular administrations. Such compounding is done by methods well known in the pharmacist's art.

The compounds of this invention and their tautomers also exhibit anti-inflammatory activity. For example, when they are administered orally to laboratory animals such as rats at a dose of 100 mg/kg, they are capable of reducing the swelling in their paws induced by the injection of an irritant such as carrageenin.

According to the present invention, the above compounds are prepared in accordance with the following reaction scheme:

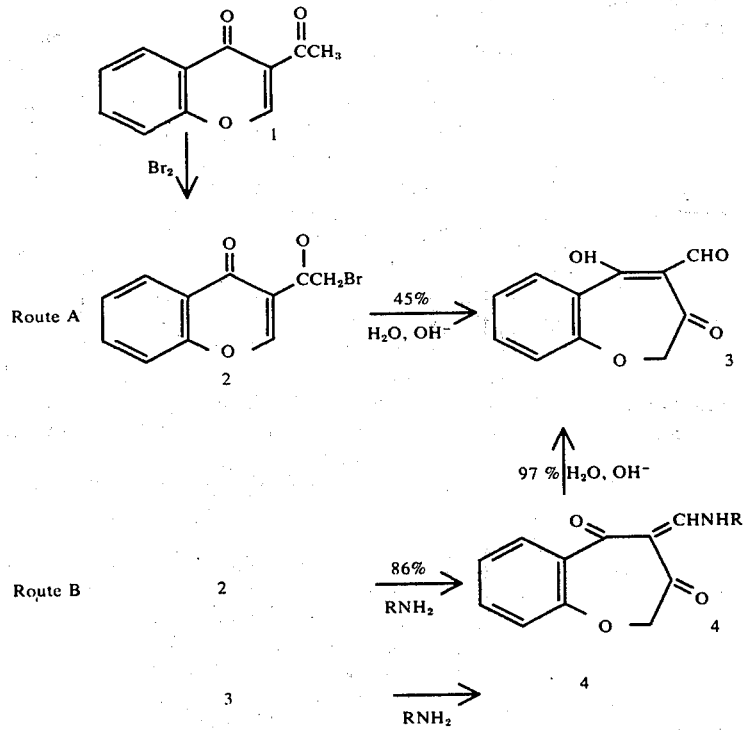

-continued

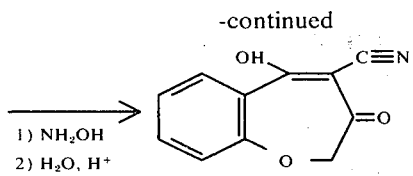

Referring now to the above scheme, compound 2 undergoes a novel base rearrangement to the 1-benzoxepin aldehyde, 3. The rearrangement is accomplished by two separate routes. Route A involves direct conversion of 2 to 3, using a strong aqueous inorganic base, e.g., NaOH or KOH. Route B, the preferred method of preparation of 3, is a two-step reaction involving firstly, rearrangement of 2 with concentrated ammonium hydroxide to the vinylogous amide 4 (R = H) and secondly, a base hydrolysis of 4 to 3. Other amine derivatives, 4, are prepared by varying the amine in the rearrangement of 2 or by the direct interaction of the aldehyde, 3, and various amines. Compounds of Type I, X= -C≡N, 5, are synthesized by treating the aldehyde, 3, with hydroxylamine and when with aqueous inorganic base.

As pointed out above, the present compounds may exist in tautomeric form. For example, when X is —CHO or —C≡N, the following tautomers exist:

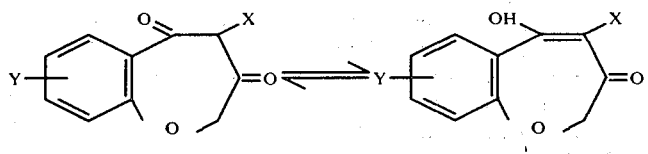

These tautomers are included within the scope of this invention.

Starting compound 2 utilized in the instant invention is prepared by brominating a known 3-acetyl chromone. Please see F. Eiden and H. Haverland, *Arch. Pharm.*, 300, 806 (1967).

The present compounds differ from known compounds in this class such as those described by Hofmann, *Angew. Chem.*, 4, 872 (1965); J.H.P. Tyman and R. Pickles, *Tetrahedron Lett.*, 41, 4993 (1966), in the following manner:

Hofmann discloses compounds containing a phenyl substituent at position 4, whereas Tyman and Pickles dealt with compounds unsubstituted at position 4. No biological activity was reported with respect to these compounds. Additionally, methods of preparation of the known compounds were different from that disclosed in the present invention. For example, the papers do not teach a method whereby a reactive formyl function can be introduced at position 4. Such an introduction is significant because it allows the preparation of various derivatives of the present invention and annelated heterocyclic compounds that have pharmacological acitivity. (See copending application, Ser. No. 554,841 filed Mar. 3, 1975.

In the above definitions for Y and in the claims hereafter, lower alkyl and the alkyl position of lower alkoxy are meant to include straight- or branched-chain alkyl groups of 1–6 carbon atoms such as methyl, ethyl, propyl, isopropyl and the like. Aryl is preferably a monocyclic aromatic ring having 6–10 carbon atoms such as phenyl and substituted phenyl.

In order to further illustrate the practice of this invention, the following examples are included. In the examples, temperatures are in degrees Centrigrade.

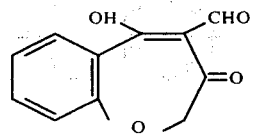

2,3-Dihydro-5-hydroxy-3-oxo-1-benzoxepin-4-carboxaldehyde.

Route A.

A mixture of 12.0g (0.045 mole) of 3-(bromoacetyl)-chromone and 400ml of 1N sodium hydroxide was heated with stirring on the steam bath. The resulting dark solution was kept at 65°–70° for 5 minutes. Ice (500G) was added, and the solution was acidified with conc. hydrochloric acid to precipitate the tacky product. This was taken-up into 300ml methylene chloride, charcoaled, filtered and concentrated; wt. 7.0g crude crystals. Recrystallization from isopropyl ether gave 4.1g (45%) pure product; m.p. 110°–112°.

Anal. Calcd. for $C_{11}H_8O_4$: C, 64.70; H, 3.95. Found: C, 64.88; H, 4.08.

Route B.

A quantity of 70.0g (0.35 mole) of 4-(aminomethylene)-1-benzoxepin-3,5(2H, 4H)-dione was added to 1400ml of 1N sodium hydroxide with stirring. The mixture was warmed to 40°. The solid gradually dissolved as ammonia was liberated. The dark, reddish-brown solution was kept at 40° for 10 minutes and filtered to remove traces of solid. Ice (500g) was added, and the filtrate was acidified to pH 1 with conc. hydrochloric acid. The separated tan solid was filtered, washed well with water and dried; wt. 68g (97%); m.p. 108°–110°. Recrystallization from isopropyl ether gave pure, peach colored crystals, m.p. 110°–112°.

Anal. Calcd. for $C_{11}H_8O_4$: C, 64.70; H, 3.95. Found: C, 64.83; H, 4.08.

EXAMPLE 2

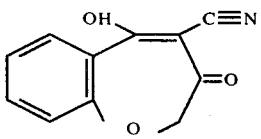

2,3-Dihydro-5-hydroxy-3-oxo-1-benzoxepin-4-carbonitrile.

To a slurry of 24.48g (0.12 mole) of 2,3-dihydro-5-hydroxy-3-oxo-1-benzoxepin-4-carboxaldehyde in 1 l. of water was added 130ml (0.13 mole) mole) of 1 N sodium hydroxide. The resulting solution was treated with a solution of 9.04g (0.13 mole) of hydroxylamine hydrochloride in 40ml of water. Solid separated. Methanol (400ml) was added, and the mixture was heated to reflux. After most solid went into solution, a new solid began to separate. After 10 minutes at reflux, the mixture was cooled, filtered and the filter cake (crude, intermediate isoxazole derivative) was washed well with water and dried; wt. 20g (78%); m.p. 109°–111°. This isoxazole derivative was warmed with 1 N sodium hydroxide (250ml) at 60° with stirring until solution was complete (ca. 5 minutes). Ice chips (300g) were added, and the solution was made strongly acid with conc. hydrocloric acid. The separated tan solid was collected, washed with ca. 50ml of cold water and dried wt. 8.5g (88%); m.p. 204°–206°. Recrystallization from methanol gave pure nitrile; m.p. 210°–212°.

Anal. Calcd. for $C_{11}H_7NO_3$: C, 65.67; H, 3.51; N, 6.96. Found: C, 65.80; H, 3.61; N, 6.83.

EXAMPLE 3

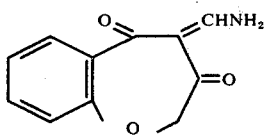

4-Aminomethylene)-1-benzoxepin-3,5(2H, 4H)-dione.

Concentrated ammonium hydroxide (1300m;) was added to a stirred mixture of 108G (0.041 mole) of 3-(bromoacetyl)chromone and 500ml of methanol. All solid went into solution. There was a mild exotherm. After several minutes the product began to separate. After one hour, the reddish-tan solid was filtered, washed well with water and dried; wt. 70g (86%); m.p. 149°–151°. Recrystallization from ethyl acetate gave pure, orange crystals; m.p. 151°–153°.

Anal. Calcd. for $C_{11}H_9NO_3$: C, 65.02; H, 4.46; N, 6.89. Found: C, 65.03; H, 4.56; N, 6.88.

EXAMPLE 4

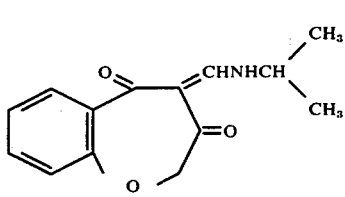

2,4-Dihydro-4-([(1-metylethyl)amino]methylene-1-benzoxepin-3,5-dione.

A mixture of 8.0g (0.03 mole) of 3-(bromoacetyl)chromone, 3.78g (0.064 mole) of isopropylamine, 200ml of methylene chloride and 30g of powdered anhydrous potassium carbonate was stirred at room temperature for 4 hours. The solids were filtered and the dark filtrate was filtered through layer of silica gel. This filtrate was concentrated to dryness. Recrystallization from ether gave 5.0g (68%) of product; m.p. 89°–91°. Recrystallization from isopropyl ether gave pure product; m.p. 92°–93°.

Anal. Calcd. for $C_{14}H_{15}NO_3$: C, 68.55; H, 6.16; N, 5.71. Found: C, 68.54; H, 6.21; N, 5.79.

EXAMPLE 5

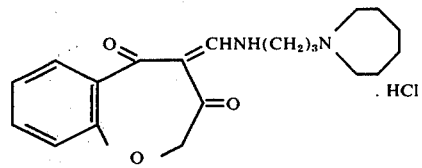

2,4-Dihydro-4-[([3-(1-piperidinyl]propyl]amino)methylene]-1-benzoxepin-3,5-dione hydrochloride.

A mixture of 8.0g (0.03 mole) of 3-(bromoacetyl)chromone, 4.54g (0.032 mole) of piperidinopropylamine, 20g powdered potassium carbonate and 200ml of methylene chloride was stirred vigorously at room temperature for one hour. The red mixture was filtered, and the filtrate was washed well with water to remove the unreacted diamine. The organic phase was dried ($K_2CO_3$) and concentrated. The residue was taken-up into ether, and the solution was treated with excess hydrogen chloride to precipitate the crude hydrochloride salt. The ether was decanted, and the residue was dissolved in 100ml of warm 2-propanol. Upon addition of ether, crystals separated; wt. 3.8g (35%) of hygroscopic salt; m.p. 157°–159°. Recrystallization from ethanol-ether gave pure product; m.p. 158°–160°.

Anal. Calcd. for $C_{19}H_{24}N_2O_3 \cdot HCl$: C, 62.55; H, 6.91; N, 7.68. Found: C, 62,42; H, 6.85; N, 7.48.

EXAMPLE 6

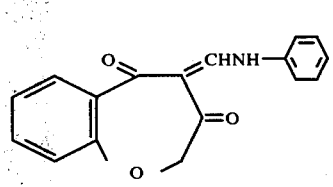

2,4-Dihydro-4-[(phenylamino)methylene]-1-benzoxepin-3,5-dione.

A quantity of 10.0g (0.049 mole) of 2,3-dihydro-5-hydroxy-3-oxo-1-benzoxepin-4-carboxaldehyde was added to 15g of aniline. The temperatuure rose to 45° as most solid went into solution. The dark mixture was heated at 105°–110° for 10 minutes and cooled. Ether (500ml) and 300ml of cold 2N hydrochloric acid were added, and the mixture was stirred for 5 minutes. The entire mixture was filtered to remove the dark, suspended insolubles. The ether phase of the filtrate was washed well with water, dried ($Na_2SO_4$) and concentrated to give 8.0g (58%) of crude product; m.p. 94°–96°. Recrystallization from ethyl acetate gave pure, orange-tan crystals; m.p. 98°–100°.

Anal. Calcd. for $C_{17}H_{13}NO_3$: C, 73.11; H, 4.69; N, 5.02. Found: C, 73.11; H, 4.68; N, 5.06.

EXAMPLE 7

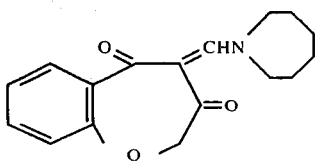

2,4-Dihydro-4-(piperidinomethylene)-1-benzoxepin-3,5-dione.

A solution of 10.2g (0.05 mole) of 2,3-dihydro-5-hydroxy-3-oxo-1-benzoxepin-4-carboxaldehyde, 5.12g (0.06 mole) of piperidine and 250ml of benzene was heated at reflux using a Dean-Stark trap. The theory of water came over in the first 10 minutes. After one-half hour the solution was cooled, ether (200ml) was added and the excess piperidine was extracted away with 200ml of 0.1N hydrochloric acid. After washing well with water the ether solution was dried (K₂CO₃) and concentrated to leave 13g of an amber, taffy-like material that could not be crystallized nor satisfactorily distilled. Thin layer chromatography (Ethylacetate-silica gel system) showed a single spot at $R_f$ 0.3.

Anal. Calcd. for $C_{16}H_{17}NO_3$: C,70.83; H, 6.32;N, 5.16. Found: C, 70.44; H, 6.46; N, 4.75.

EXAMPLE 8

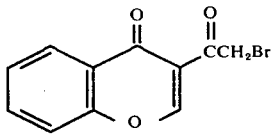

3-(Bromoacetyl)chromone.

A solution of 1.6g (0.01 mole) of bromine in 10ml of chloroform was added over a period of 5 minutes to a stirred solution of 1.88g (0.01 mole) of 3-acetylchromone. [RE: F. Eiden and H. Havenland, Arch. Pharm., 300, 806 (1967)]. After one-half hour the solvent was removed to give 1.9g (70%) of crude product; m.p. 140°–145°. Recrystallization from ethyl acetate gave pure product; m.p. 151 –153°.

Anal. Calcd. for $C_{11}H_7BrO_3$: C, 49.47; H, 2.64; Br, 29.92. Found: C, 49.57; H, 2.88; Br, 30.20.

We claim:
1. A compound of the formula:

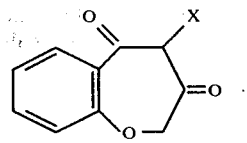

wherein X is

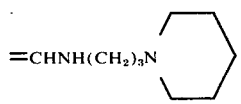

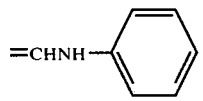

or

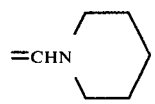

and tautomers thereof.

2. A compound according to claim 1 which is 2,4-dihydro-4-[([3-(1-piperidinyl)propyl]amino)methylene]-1-benzoxepin-3,5-dione.

3. A compound according to claim 1 which is 2,4-dihydro-4-[(phenylamino)methylene]-1-benzoxepin-3,5-dione.

4. A compound according to claim 1 which is 2,4-dihydro-4-(piperidinomethylene)-1-benzoxepin-3,5-dione.

* * * * *